United States Patent
Roldán-Alzate et al.

(10) Patent No.: US 11,181,601 B1
(45) Date of Patent: Nov. 23, 2021

(54) SYSTEMS AND METHODS FOR MAGNETIC RESONANCE PHANTOMS

(71) Applicant: Wisconsin Alumni Research Foundation, Madison, WI (US)

(72) Inventors: Alejandro Roldán-Alzate, Madison, WI (US); David Rutkowski, Madison, WI (US); Diego Hernando Arribas, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/878,399

(22) Filed: May 19, 2020

(51) Int. Cl.
*G01R 33/58* (2006.01)
*G01R 33/30* (2006.01)
*A61B 5/00* (2006.01)
*A61B 5/055* (2006.01)

(52) U.S. Cl.
CPC ............ *G01R 33/58* (2013.01); *G01R 33/30* (2013.01); *A61B 5/055* (2013.01); *A61B 5/4244* (2013.01)

(58) Field of Classification Search
USPC ........................................................ 324/18
See application file for complete search history.

(56) References Cited

U.S. PATENT DOCUMENTS

| | | | |
|---|---|---|---|
| 4,729,892 A | 3/1988 | Beall | |
| 5,196,343 A | 3/1993 | Zerhouni | |
| 7,462,488 B2 * | 12/2008 | Madsen | A61B 5/055 422/536 |
| 9,880,251 B2 | 1/2018 | Kerins | |
| 2008/0261009 A1 * | 10/2008 | Kawabata | A61B 8/00 428/217 |
| 2012/0068699 A1 * | 3/2012 | Horkay | A61B 5/418 324/300 |
| 2017/0192077 A1 | 7/2017 | Dzyubak | |

FOREIGN PATENT DOCUMENTS

| | | |
|---|---|---|
| CN | 101864136 A | 10/2010 |
| JP | 2014223546 A | 12/2014 |
| JP | 2018041055 A | 3/2018 |
| WO | 2004032706 A2 | 4/2014 |
| WO | 2019180464 A1 | 9/2019 |

OTHER PUBLICATIONS

Arunachalam SP, et al. Quantitative 3D magnetic resonance elastography: Comparison with dynamic mechanical analysis. Magn Reson Med 2017;77(3):1184-1192.

Cao, Y, et al. "Tissue-mimicking materials for elastography phantoms: A review." Extreme Mechanics Letters 17 (2017): 62-70.

(Continued)

*Primary Examiner* — Rodney E Fuller
(74) *Attorney, Agent, or Firm* — Quarles & Brady LLP

(57) ABSTRACT

In some embodiments, the present disclosure discloses a magnetic resonance (MR) phantom. The MR phantom includes a housing, a base medium disposed within the housing, and one or more compartment extending through the base medium, the one or more compartment comprising a crosslinked acrylamide-based polymer. The MR phantoms may be used as calibration phantoms for magnetic resonance elastography sequences and diffusion weighted images.

21 Claims, 4 Drawing Sheets

(56) References Cited

OTHER PUBLICATIONS

Gordon-Wylie SW, et al. MR elastography at 1 Hz of gelatin phantoms using 3D or 4D acquisition. J Magn Reson 2018;296:112-120.

Guidetti M, et al. Anisotropic composite material phantom to improve skeletal muscle characterization using magnetic resonance elastography. J Mech Behav Biomed Mater 2019;89:199-208.

Hall, T. J., et al. "Phantom materials for elastography." IEEE transactions on ultrasonics, ferroelectrics, and frequency control 44.6 (1997): 1355-1365.

Kandow, C. E., et al. "Polyacrylamide hydrogels for cell mechanics: steps toward optimization and alternative uses." Methods in cell biology 83 (2007): 29-46.

Kashif AS, et al. Silicone breast phantoms for elastographic imaging evaluation. Med Phys 2013;40(6):063503.

Kaufman JD, et al. Time-dependent mechanical characterization of poly(2-hydroxyethyl methacrylate) hydrogels using nanoindentation and unconfined compression. J Mater Res 2008;23(5):1472-1481.

Leclerc, G. E., et al. "Characterization of a hyper-viscoelastic phantom mimicking biological soft tissue using an abdominal pneumatic driver with magnetic resonance elastography (MRE)." Journal of biomechanics 45.6 (2012): 952-957.

Madsen, E. L., et al. "Anthropomorphic breast phantoms for testing elastography systems." Ultrasound in medicine & biology 32.6 (2006): 857-874.

Manduca A, et al. Magnetic resonance elastography: non-invasive mapping of tissue elasticity. Med Image Anal 2001;5(4):237-254.

Mariappan YK, et al. High-frequency mode conversion technique for stiff lesion detection with magnetic resonance elastography (MRE). Magn Reson Med 2009;62(6):1457-1465.

Minton JA, et al. Improving the homogeneity of tissue-mimicking cryogel phantoms for medical imaging. Med Phys 2012;39(11):6796-6807.

Morisaka H, et al. Comparison of diagnostic accuracies of two- and three-dimensional MR elastography of the liver. J Magn Reson Imaging 2017;45(4):1163-1170.

Resoundant. MRE Phanton User Guide. 2016. 8 pages.

Sheth, S., et al. "UV Dose Governs UV-Polymerized Polyacrylamide Hydrogel Modulus." International Journal of Polymer Science 2017 (2017).

Solamen LM, et al. Phantom evaluations of low frequency MR elastography. Phys Med Biol 2019;64(6):065010.

Solamen LM, et al. Phantom evaluations of nonlinear inversion MR elastography. Phys Med Biol 2018;63(14):145021.

\* cited by examiner

SYSTEMS AND METHODS FOR MAGNETIC RESONANCE PHANTOMS

STATEMENT REGARDING FEDERALLY SPONSORED RESEARCH

This invention was made with government support under DK117354 and EB025729 awarded by the National Institutes of Health. The government has certain rights in the invention.

BACKGROUND

Medical imaging is a fundamental resource in the modern practice of clinical medicine. The ability to acquire anatomical, physiological, and pathological information about the patient non-invasively makes medical imaging ubiquitous in many clinical applications. Furthermore, medical imaging can be used to direct and deliver therapeutic or surgical procedures.

In all of these settings, medical imaging provides powerful resources for the practice of clinical medicine by providing the ability to secure patient-specific information. However, medical imaging often struggles when looking to assess information across patients, or even longitudinally for a given patient. This occurs because medical imaging systems reflect a great deal of variability, such as between imaging modalities, system manufacturers, clinical implementations, or the like.

For example, magnetic resonance imaging (MM) is well established as the gold standard for acquiring clinical data in a wide-variety of clinical applications. However, images of the same patient, even using the same type of MRI study, across different MRI systems can vary greatly. As just one example, a diffusion weighted imaging (DWI) study of the same patient performed at two different times using two different MRI systems, even when the MM systems were manufactured by the same manufacturer, can yield two very-different images, even when the underlying anatomy and physiology is unchanged.

Furthermore, increasing the complexity of the study, such as to include additional hardware systems that are coordinated with the MM system, such as is the case in magnetic resonance elastography (MRE), can further increase the variability caused by differences in systems, manufacturers, or even the technicians or clinicians involved in the studies.

Thus, there continues to be a need for systems and methods to facilitate the consistency and quality of medical imaging data and studies.

SUMMARY OF THE INVENTION

The present disclosure provides systems and methods for improving the operation, quality, and/or consistency of performing a magnetic resonance (MR) study by providing phantom systems and methods of operation that can be used with a variety of MR application, such as magnetic resonance elastography sequences and diffusion weighted imaging. A phantom may a comprise housing, a base medium disposed within the housing, and one or more compartment extending through the base medium. The one or more compartment may include a crosslinked acrylamide-based polymer.

In some configurations, the present disclosure provides a magnetic resonance phantom comprising a sealed compartment and a hydrogel disposed in the sealed compartment. The hydrogel comprises a crosslinked acrylamide-based polymer and a solvent, the crosslinked acrylamide-based polymer comprising (i) at least 50 wt % of a polymerized acrylamide monomer, based on the total weight of the acrylamide-based polymer; and (ii) less than 10 wt % of a crosslinking agent, based on the total weight of the crosslinked acrylamide-based polymer.

These and other advantages and features of the invention will become more apparent from the following detailed description of the preferred embodiments of the invention when viewed in conjunction with the accompanying drawings.

DETAILED DESCRIPTION

Figure 1:
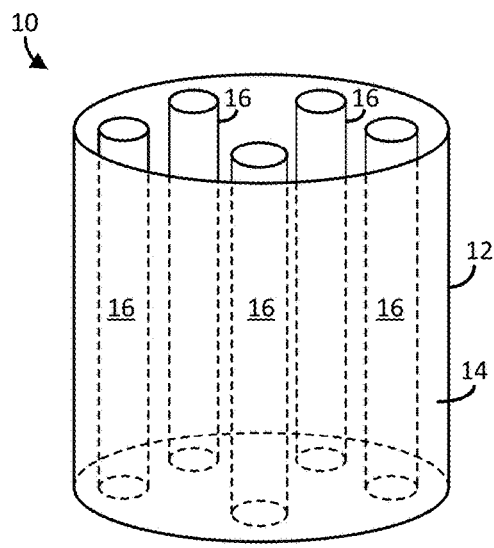
FIG. 1 is perspective view of a magnetic resonance (MR) phantom apparatus in accordance with some embodiments of the present disclosure.

As noted above, magnetic resonance imaging (MRI) is a highly-valuable resource in the practice of modern clinical medicine. MRI finds application is a very-wide variety of clinical settings. For example, chronic liver disease (CLD) is one of the leading causes of death in the United States and is a major public health burden. Early detection and disease tracking through liver biopsy can help prevent fibrosis progression and better inform treatment planning. However, biopsy procedures carry non-negligible risk, and are prone to high rates of sampling error and observer variability. MRI can be used as a tool to study CLD.

In particular, elastography, or elasticity imaging, has emerged as a viable alternative for analysis of liver fibrosis. Original elastography methods were performed with ultrasound imaging. However, ultrasound elastography has a number of limitations specific to the CLD population and tends to have high failure rates. Magnetic Resonance Elastography (MRE) is an MRI-based alternative that has demonstrated higher diagnostic accuracy than ultrasound elastography. MRE is currently known as one of the most accurate non-invasive methods for identifying, diagnosing, and tracking liver fibrosis, according to a number of professional organizations and associations and can be easily added to the end of a clinical MRI exam. However, like other quantitative biomarkers, a reference standard for liver stiffness measurement is needed for quality assurance (QA) in imaging studies and facilitate consistency, across studies, including across hardware platforms and the like.

As another example, diffusion weighted imaging (DWI) is an MRI method to evaluate the molecular function and micro-architecture of the human body. DWI signal contrast can be quantified by apparent diffusion coefficient maps and it acts as a tool for treatment response evaluation and assessment of disease progression. Ability to detect and quantify the anisotropy of diffusion leads to a new paradigm called diffusion tensor imaging (DTI). DTI is a tool for assessment of the organs with highly organized fiber structure. DWI forms an integral part of modern state-of-art magnetic resonance imaging and is indispensable in neuro-imaging and oncology. DWI is a field that has been undergoing rapid technical evolution and its applications are increasing every day. Here too, improved standards are needed to achieve quality assurance (QA) in imaging studies and facilitate consistency, across studies, including across hardware platforms and the like.

The present disclosure provides a magnetic resonance (MR) phantom apparatus. As will be described, the MR phantom apparatus of the present disclosure provides substantial advantages over traditional phantoms. For example, traditional phantoms suffer from "drift" or variability over time as the materials of the phantom change, such as dehydrating or the like. Some phantoms lack dynamic range, form healthy to pathological ranges. Also, phantoms struggle to mimic both the anatomical and physiological conditions that are the focus of particular imaging studies. The MR phantom systems and methods provided herein overcome these shortcomings to provide substantial improvements for a variety of clinical applications, such as MRE and DWI.

Figure 2:
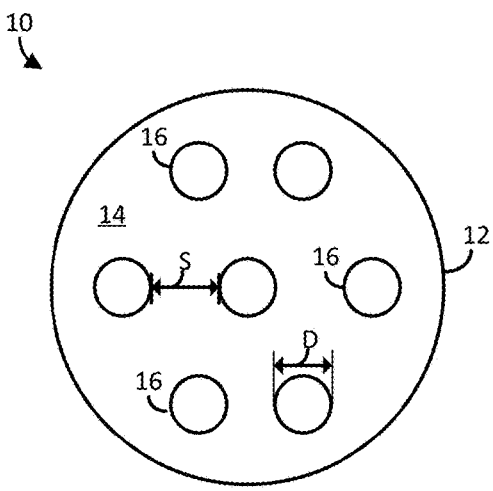
FIG. 2 is top, cross-sectional view of a MR phantom apparatus in accordance with some embodiments of the present disclosure.

Referring to FIGS. 1-2, one example of a MR phantom apparatus 10 in accordance with the present disclosure is shown. The MR phantom apparatus 10 includes a housing 12 having a base medium 14 disposed within the housing 12, and one or more compartment 16 extending through the base medium 14.

In some configurations, the housing 12 includes walls that form a geometric shape and enclose an interior volume. Exemplary geometric shapes include, but are not limited to, a sphere, a cylinder, regular and irregular prisms, such as triangular prisms, cube prisms, rectangular prisms. In some configurations, the housing 12 has a cross-sectional shape that is an ellipse. Non-limiting example ellipse shapes include circle, oval, and ovoid. In some embodiments, the housing 12 is composed of a transparent plastic. Example transparent plastics include, but are not limited to, acrylic and polycarbonate.

In some configurations, the housing 12 includes one or more compartments 16 composed of a polymer matrix material. As used herein, the term "polymer" may refer to a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymers, e.g., random, block, etc. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to has being based on "units" that are the polymerized form of a corresponding monomer.

In some configurations, the one or more compartments 16 may include a crosslinked acrylamide-based polymer. As used herein, the term "acrylamide-based polymer" may refer to a polymer that contains one or more polymerized acrylamide monomer and, optionally, may contain at least one comonomer. The terms "acrylamide-based polymer" and "polyacrylamide" may be used interchangeably.

As used herein, the phrase "crosslinked polymer" may refer to a polymer that contains a monomer (e.g., acrylamide) that has been copolymerized with one or more crosslinking agent comonomer (e.g., N—N'-methylene-bis-acrylamide or "bis"). Suitable crosslinking agents include bifunctional comonomer reagents that induce crosslinks, or covalent bonds, between linear polyacrylamide chains creating a network of covalently bonded polyacrylamide, rather than unconnected linear chains of polyacrylamide. As used herein, the terms "acrylamide/crosslinking agent" or "acrylamide/N—N'-methylene-bisacrylamide" may be indicative of a copolymer as described above prepared from polymerizing an acrylamide monomer with one or more crosslinking comonomer. Such a process may be induced using activating agents such as tetramethyl ethylenediamine (TEMED) and ammonium persulfate.

In some configurations, the polymerized acrylamide monomer constitutes greater than 50 wt % based on the total weight of the crosslinked acrylamide-based polymer. In some configurations, the polymerized acrylamide monomer constitutes from 50 wt % to 99 wt % based on the total weight of the crosslinked acrylamide-based polymer. In some configurations, the polymerized acrylamide monomer constitutes at least 50 wt %, or at least 55 wt %, or at least 60 wt %, or at least 65 wt %, or at least 70 wt %, or at least 75 wt %, or at least 80 wt %, or at least 85 wt %, or at least 90 wt %, to less than 91 wt %, or less than 92 wt %, or less than 93 wt %, or less than 94 wt %, or less than 95 wt %, or less than 96 wt %, or less than 97 wt %, or less than 98 wt %, or less than 99 wt %, based on the total weight of the crosslinked acrylamide-based polymer.

In some configurations, the crosslinking agent constitutes less than 10 wt % based on the total weight of the crosslinked acrylamide-based polymer. In some configurations, the crosslinking agent constitutes from 0.01 wt % to 10 wt %. In some configurations, the crosslinking agent constitutes at least 0.1 wt %, or at least 0.5 wt %, or at least 1 wt %, or at least 1.5 wt %, or at least 2 wt %, or at least 2.5 wt %, or at least 3 wt %, or at least 3.5 wt %, or at least 4 wt %, or at least 4.5 wt %, or at least 5 wt %, to less than 5.5 wt %, or less than 6 wt %, or less than 7 wt %, or less than 8 wt %, or less than 9 wt %, or less than 10 wt %, based on the total weight of the crosslinked acrylamide-based polymer.

In some configurations, acrylamide-based polymer is a hydrogel. As used herein, a "hydrogel" may refer to insoluble, crosslinked, three-dimensional networks of polymer chains having a solvent or dispersing medium that fills the voids between the polymer chains. In some configurations, the solvent or dispersing medium includes, but is not limited to, water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, fetal bovine serum, or suitable combinations and/or mixtures thereof.

In some configurations, the hydrogel in the one or more compartment 16 has a solvent or dispersing medium content from 50 wt % to 99.99 wt %, based on the total weight of the hydrogel. In some configurations, varying the solvent or dispersing medium content alters the mechanical stiffness or diffusion properties of the acrylamide-based polymer. In some configurations, the hydrogel has a solvent or dispersing medium content of at least 50 wt %, or at least 55 wt %, or at least 60 wt %, or at least 65 wt %, or at least 70 wt %, or at least 75 wt %, or at least 80 wt %, or at least 85 wt %, or at least 90 wt %, to less than 91 wt %, or less than 92 wt %, or less than 93 wt %, or less than 94 wt %, or less than 95 wt %, or less than 96 wt %, or less than 97 wt %, or less than 98 wt %, or less than 99 wt %, or less than 99.5 wt %, or less than 99.9 wt %, or less than 99.99 wt %, based on the total weight of the hydrogel.

In some configurations, the hydrogel in the one or more compartment 16 has an acrylamide-based polymer content from 0.01 wt % to 50 wt %, based on the total weight of the hydrogel. In some configurations, the hydrogel has an acrylamide-based polymer content of at least 0.01 wt %, or at least 0.05 wt %, or at least 0.1 wt %, or at least 0.5 wt %, or at least 1 wt %, or at least 2 wt %, or at least 3 wt %, or at least 4 wt %, or at least 5 wt %, or at least 6 wt %, or at least 7 wt %, or at least 8 wt %, or at least 9 wt %, or at least 10 wt %, to less than 11 wt %, or less than 12 wt %, or less than 13 wt %, or less than 14 wt %, or less than 15 wt %, or less than 20 wt %, or less than 30 wt %, or less than 40 wt %, or less than 50 wt %, based on the total weight of the hydrogel.

In some configurations, one or more of the compartments 16 may be a control compartment. The control compartment may include solvent or dispersing medium. In some configurations, the control compartment 16 is free of acrylamide-based polymers. In some configurations, the control compartment 16 consists only of solvent or dispersing medium.

Referring back to FIGS. 1-2, the MR phantom apparatus 10 may include a plurality of compartments 16 having varying concentrations of acrylamide-based polymer and solvent or dispersing medium. Each compartment 16 may have a known mechanical stiffness or diffusion property (e.g., apparent diffusion coefficient). The MR phantom apparatus 10 can then be scanned by an MRI apparatus using imaging sequences, such as diffusion weighted imaging (DWI) or and magnetic resonance elastography images for various applications, such as calibrating the MM apparatus (e.g., using the phantom apparatus to calibrate "measured" parameters to "corrected" parameters), to perform clinical quality assurance, to perform site qualification for multicenter trials, or to aid in technical development and evaluation of new MRI procedures.

In some configurations, the MR phantom apparatus 10 contains at least two compartments 16. In some configurations, the MR phantom apparatus 10 contains from 2 to 50 compartments 16, or more. In some configurations, the MR phantom apparatus 10 contains at least 2 compartments 16, or at least 3, or at least 4, or at least 5, or at least 6, or at least 7, or at least 8, or at least 9, to at least 10, or less than 15, or less than 20, or less than 25, or less than 30, or less than 35, or less than 40, or less than 45, or less than 50 compartments 16.

In some configurations, each compartment 16 contains a different concentration of the acrylamide-based polymer. In some configurations, the compartments 16 form an array of concentrations that ranges from greater than, or equal to, 0 wt % to less than 50 wt % acrylamide-based polymer based on the total weight of components in each compartment in the array, or from greater than, or equal to, 0 wt % to less than, or equal to, 45 wt %, or from greater than, or equal to, 0 wt % to less than 40 wt %, or from greater than, or equal to, 0 wt % to less than 35 wt %, or from greater than, or equal to, 0 wt % to less than 30 wt %, or from greater than, or equal to, 0 wt % to less than 25 wt %, or from greater than, or equal to, 0 wt % to less than 20 wt %, or from greater than, or equal to, 0 wt % to less than 15 wt %, or from greater than, or equal to, 0 wt % to less than 10 wt %, or from greater than, or equal to, 0 wt %, to less than 5 wt %, based on the total weight of components in each compartment in the array.

In some configurations, the compartments 16 have a spacing S within the housing 12. In some configurations, the compartments 16 may or may not be evenly spaced apart within the housing 12. The spacing S may be defined as the minimum distance between the outer surfaces of two adjacent compartments 16. In some configurations, the spacing is at least 1 mm. In some configurations, the spacing is from 1 to 500 mm, or more. In some configurations, the spacing is at least 1 mm, or at least 2 mm, or at least 3 mm, or at least 4 mm, or at least 5 mm, or at least 6 mm, or at least 7 mm, or at least 8 mm, or at least 9 mm, to at least 10 mm, or less than 15 mm, or less than 20 mm, or less than 30 mm, or less than 40 mm, or less than 50 mm, or less than 60 mm, or less than 80 mm, or less than 90 mm, or less than 100 mm, or less than 200 mm, or less than 300 mm, or less than 400 mm, or less than 500 mm.

In some configurations, the compartments 16 have a geometric shape. The geometric shape of the compartments 16 may match or substantially match the geometric shape of the housing 12. In some configurations, compartments 16 have geometric shape that is, but are not limited to, a sphere, a cylinder, regular and irregular prisms, such as triangular prisms, cube prisms, rectangular prisms. In some configurations, the compartments 16 have a cross-sectional shape that is an ellipse. In some configurations, the ellipse may be a circle, oval, or ovoid. In some configurations, the compartments 16 have an anthropomorphic shape indicative of human anatomy, such as an organ. In some configurations, the compartment 16 has an anthropomorphic shape of an organ including, but not limited to, heart, lungs, liver, pancreas, esophagus, stomach, gallbladder, intestines, colon, rectum, anus, hypothalamus, pineal body, thyroid, parathyroids, adrenals, kidney, ureters, bladder, urethra, tonsils, adenoids, thymus, spleen, muscles, brain, spinal cord, ovaries, fallopian tubes, uterus, vulva, vagina, testes, vas deferens, prostate, penus, cartilage, ligaments, and tendons.

In some configurations, the compartments 16 have a physical dimension D (e.g., diameter, width, and/or length) of at least 5 mm. In some configurations, the compartments 16 have a physical dimension D from 5 mm to 500 mm, or more. In some configurations, the compartments 16 have a physical dimension D of at least 5 mm, or at least 10 mm, or at least 15 mm, or at least 20 mm, or at least 25 mm, or at least 30 mm, or at least 35 mm, or at least 40 mm, or at least 45 mm, or at least 50 mm, to less than 60 mm, or less than 70 mm, or less than 80 mm, or less than 90 mm, or less than 100 mm, or less than 200 mm, or less than 300 mm, or less than 400 mm, or less than 500 mm.

In some configurations, the one or more compartments 16 extends from 5% to 100% of the length, height, or diameter of the housing 12. In some configurations, the one or more compartments 16 extends at least 5% of the length, height, or diameter of the housing 12, or at least 10%, or at least 25%, or at least 50%, or at least 75%, to less than 80%, or less than 85%, or less than 90%, or less than 95%, or less than 99%, or to 100% of the length or height of the housing 12.

In some configurations, the one or more compartments 16 constitute at least 5% percent of the internal volume (v/v) of the housing 12. In some configurations, the one or more compartment 16 constitute from 10% to 95% of the internal volume of the housing 12. In some configurations, the one or more compartment 16 constitutes at least 10% (v/v), or at least 20%, or at least 30%, or at least 40%, or at least 50%, or at least 60%, or at least 70%, or at least 80%, or at least 90%, or at least 95% (v/v) of the internal volume of the housing 12.

In some configurations, the one or more compartments 16 may be composed of a hydrogel that is encased in a material, such as a polymeric film or glass. In some configurations, the compartments 16 may form a sealed compartment. The sealed compartment may have a hermetic seal (i.e., is airtight) and/or a watertight seal. In some configurations, the glass may completely surround the hydrogel disposed in the one or more compartments 16. In some configurations, the glass may have a re-sealable opening (e.g., a vial). Nonlimiting examples of suitable polymeric film materials include olefin-based polymers (including any ethylene/C3-C10 α-olefin copolymers linear or branched), propylene-based polymer (including plastomer and elastomer, random propylene copolymer, propylene homopolymer, and propylene impact copolymer), ethylene-based polymer (including plastomer and elastomer, high density polyethylene ("HDPE"), low density polyethylene ("LDPE"), linear low density polyethylene ("LLDPE"), medium density polyethylene ("MDPE"), ethylene-acrylic acid or ethylene-methacrylic acid and their ionomers with zinc, sodium, lithium, potassium, magnesium salts, ethylene vinyl acetate copolymers) and blends thereof.

In some configurations, the one or more compartment 16 may include a hydrogel having a material modulus from 1 kPa to 100 kPa. In some configurations, the one or more compartment 16 includes a hydrogel having a material modulus of at least 1 kPa, or at least 2 kPa, or at least 3 kPa, or at least 4 kPa, or at least 5 kPa, or at least 6 kPa, or at least 7 kPa, or at least 8 kPa, or at least 9 Kpa, or at least 10 kPa, or at least 15 kPa, to less than 20 kPa, or less than 25 kPa, or less than 30 kPa, or less than 35 kPa, or less than 40 kPa, or less than 45 kPa, or less than 50 kPa, or less than 75 kPa, or less than 100 kPa.

In some configurations, the one or more compartment 16 includes a hydrogel having an apparent diffusion coefficient (ADC) of less than $2.5\times10^{-3}$ mm$^2$/s, or in some configurations, from $0.1\times10^{-3}$ mm$^2$/s to $2.5\times10^{-3}$ mm$^2$/s. In some configurations, the one or more compartment 16 includes a hydrogel having an ADC of at least $0.1\times10^{-3}$ mm$^2$/s, or at least $0.2\times10^{-3}$ mm$^2$/s, or at least $0.3\times10^{-3}$ mm$^2$/s, or at least $0.4\times10^{-3}$ mm$^2$/s, or at least $0.5\times10^{-3}$ mm$^2$/s, or at least $0.6\times10^{-3}$ mm$^2$/s, or at least $0.7\times10^{-3}$ mm$^2$/s, or at least $0.8\times10^{-3}$ mm$^2$/s, or at least $0.9\times10^{-3}$ mm$^2$/s, or at least $1.0\times10^{-3}$ mm$^2$/s, or at least $1.1\times10^{-3}$ mm$^2$/s, or at least $1.2\times10^{-3}$ mm$^2$/s, or at least $1.3\times10^{-3}$ mm$^2$/s, or at least $1.4\times10^{-3}$ mm$^2$/s, or at least $1.5\times10^{-3}$ mm$^2$/s, or less than $1.6\times10^{-3}$ mm$^2$/s, or less than $1.7\times10^{-3}$ mm$^2$/s, or less than $1.8\times10^{-3}$ mm$^2$/s, or less than $1.9\times10^{-3}$ mm$^2$/s, or less than $2.0\times10^{-3}$ mm$^2$/s, or less than $2.1\times10^{-3}$ mm$^2$/s, or less than $2.2\times10^{-3}$ mm$^2$/s, or less than $2.3\times10^{-3}$ mm$^2$/s, or less than $2.4\times10^{-3}$ mm$^2$/s, or less than $2.5\times10^{-3}$ mm$^2$/s.

In some configurations, the MR phantom apparatus 10 includes a base medium 14. The base medium 14 may partially or completely surround the one or more compartments 16 within the internal volume of the housing 12. In some configurations, the base medium 14 is in direct contact with the one or more compartments 16 (e.g., the base medium may directly contact the hydrogel or acrylamide-based polymer in the one or more compartments 16). In some configurations, the base medium 14 contacts the side surfaces of the one or more compartments 16, but does not contact the top and/or bottom surfaces of the one or more compartments 16. In some configurations, the base medium 14 includes a plurality of channels or voids sized to receive the one or more compartments 16.

In some configurations, the base medium 14 includes a hydrogel. In some configurations, the base medium 14 includes hydrogel composed of the acrylamide-based polymer and a solvent and/or dispersing medium described above.

In some configurations, the hydrogel in the base medium 14 has a solvent or dispersing medium content from 50 wt % to 99.99 wt %, based on the total weight of the hydrogel. In some configurations, the hydrogel in the base medium 14 has a solvent or dispersing medium content of at least 50 wt %, or at least 55 wt %, or at least 60 wt %, or at least 65 wt %, or at least 70 wt %, or at least 75 wt %, or at least 80 wt %, or at least 85 wt %, or at least 90 wt %, to less than 91 wt %, or less than 92 wt %, or less than 93 wt %, or less than 94 wt %, or less than 95 wt %, or less than 96 wt %, or less than 97 wt %, or less than 98 wt %, or less than 99 wt %, or less than 99.5 wt %, or less than 99.9 wt %, or less than 99.99 wt %, based on the total weight of the hydrogel in the base medium 14.

In some configurations, the hydrogel in base medium 14 has an acrylamide-based polymer content from 0.01 wt % to 50 wt %, based on the total weight of the hydrogel. In some configurations, the hydrogel has an acrylamide-based polymer content of at least 0.01 wt %, or at least 0.05 wt %, or at least 0.1 wt %, or at least 0.5 wt %, or at least 1 wt %, or at least 2 wt %, or at least 3 wt %, or at least 4 wt %, or at least 5 wt %, or at least 6 wt %, or at least 7 wt %, or at least 8 wt %, or at least 9 wt %, or at least 10 wt %, to less than 11 wt %, or less than 12 wt %, or less than 13 wt %, or less than 14 wt %, or less than 15 wt %, or less than 20 wt %, or less than 30 wt %, or less than 40 wt %, or less than 50 wt %, based on the total weight of the hydrogel in the base medium 14.

In some configurations, the base medium 14 comprises or consists of a solvent or dispersing medium described above. In some configurations, the base medium 14 comprises or consists of a gas, such as air.

In some configurations, the base medium 14 constitutes at least 5% percent of the internal volume (v/v) of the housing 12. In some configurations, the one or more compartment 16 constitute from 10% to 95% of the internal volume of the housing 12. In some configurations, the one or more compartment 16 constitutes at least 10% (v/v), or at least 20%, or at least 30%, or at least 40%, or at least 50%, or at least 60%, or at least 70%, or at least 80%, or at least 90%, or at least 95% (v/v) of the internal volume of the housing 12.

In some configurations, the one or more compartments 16 and/or the base medium 14 comprise a contrast agent. In some configurations, the contrast agent may be present in an amount of less than 10% based on the total weight of components in the one or more compartments 16 and/or the base medium 14. Exemplary contrast agents include compounds and/or chemical moieties that enhance or alter imaging parameters (e.g., $T_1$ and/or $T_2$) during MM imaging. Exemplary contrast agents include salts, such as sodium chloride, nickel chloride, magnesium chloride, copper sulfate, and combinations thereof.

Figure 3:
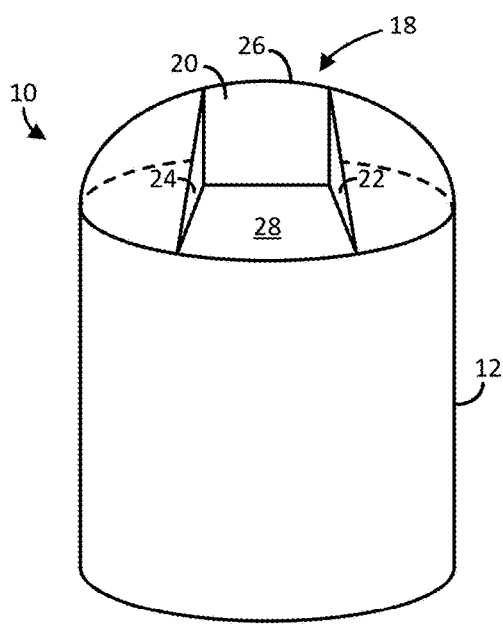
FIG. 3 is a perspective view of a MR phantom in accordance with some embodiments of the present disclosure.

Referring now to FIG. 3, a housing 12 is illustrated for the MR phantom apparatus 10 according to some configurations of the present disclosure. The housing 12 includes a recessed region 18. The recessed region 18 may be sized to receive a passive driver for MRE imaging. In MRE imaging, active drivers are responsible for generating mechanical waves, which are transmitted to the region of interest on the patient by a passive driver connected to the active drive through a tube (e.g., plastic tube). In some configurations, the recessed region 18 is arranged such that the passive driver can transmit mechanical waves to the one or more compartments 16.

FIG. 3 illustrates an exemplary recessed region 18 according to some configurations of the present disclosure. The recessed region 18 may include a central wall 20 that connects two opposing side walls 22, 24. The walls 18, 22, and 24 extend from an outer surface 26 towards the internal volume of the housing 12 to a base wall 28 or "seat portion" for receiving the passive driver. In some configurations, the base wall 28 or seat portion is parallel to the top and/or bottom surface of the one or more compartments 16.

Although not illustrated in FIG. 3, the recessed region 18 may have different geometric shapes. For example, the recessed region may have a prism as a geometric shape. Suitable prisms may form at least 3 interior faces in the housing 12 (e.g., a recessed region 18 formed from 3 walls extending toward the interior volume of the housing 12, forming a triangular prism cut away shape), or at least 4 interior faces (e.g., a cube-like or rectangular-like recessed region similar to that illustrated in FIG. 3), or to at least 5 interior faces (e.g., a slotted shape having two opposing surfaces and a back wall), or more faces. Each geometric shape may have at least one face that is parallel to the top and/or bottom surfaces of the one or more compartments 16. The recessed region 18 may be sized so that the passive driver may be moved above each of the one or more compartments 16.

EXAMPLES

The following examples are presented by way of illustration and are not meant to be limiting in any way.

MRE Phantom:

An MRE phantom with 5 compartments of varied mechanical stiffness was fabricated with polyacrylamide hydrogel. The hydrogel material base solution was created by dissolving two polymer components-acrylamide and bisacrylamide (Fisher Scientific, Hampton, N.H., USA)- into de-ionized water. The stiffness of the hydrogel samples was varied by changing the percentage of polymer components dissolved in the water base. Gel percentages of each sample included in the phantom were 4%, 6%, 8%, and 10%. Cross-linking of the gel was initiated by the addition of Tetramethylethylenediamine (TEMED) and ammonium persulfate (Fisher Scientific, Hampton, N.H., USA).

Four hydrogel compartments were created by filling custom 3D-printed cylindrical molds with hydrogel of different stiffness properties. Portions of each sample material, along with additional samples of 12% and 16% gel, were poured into a separate container for later mechanical testing. The four cylinders were placed in a sealed, acrylic housing (7"×4") and surrounded by a fifth hydrogel of 6% gel composition. A cylindrical void of water was also included in the phantom.

MRE Images:

MRE stiffness images were obtained using a single-shot spin echo EPI pulse sequence on a 3T imaging system (SIGNA Premier, GE Healthcare, Waukesha, Wis.) using a 30 channel AIR™ coil and 60-channel posterior coil: scan time=5 min; TR=3000 ms; TE=71 ms; phase offsets=8; vibration frequency=60 Hz; vibration amplitude=50% max; slice thickness=3 mm; matrix=80×80. Mechanical vibrations were introduced using a soft, pillow-like driver through a pneumatic actuator (Resoundant, Rochester, Minn.). The phantom was placed on the pillow driver such that the cylinders were running vertically. MRE stiffness maps were obtained using a 3D direct inversion reconstruction. Regions of interest (ROI) measurements were manually drawn over all cylinders (including background material) in Matlab (Mathworks, Natick, Mass.).

Mechanical Analysis:

The hydrogel samples that were set aside during phantom fabrication were mechanically tested in unconfined compression and dynamic mechanical analysis. Cylindrical samples were made using biopsy punches on existing samples and by casting additional gels into 3D printed custom cylindrical molds. For unconfined compression testing, sample thickness was measured using calipers and samples were placed between two glass plates on a tabletop test machine equipped with a 1 kg load cell. A small tare load was applied, followed by a ramp to 10% strain at 0.10 s−1. Following testing, engineering strain and first Piola-Kirchhoff stress were calculated. A linear modulus was fit to the stress-strain data using custom MatLab code. Dynamic mechanical analysis was performed by applying an oscillatory strain to a sample and measuring the resulting sinusoidal stress with a Rheometrics Series RSA III system. From the stress magnitude, and corresponding phase delay from the input, the viscoelastic properties of the sample were recorded.

Figure 4:
FIG. 4 are magnetic resonance elastography images taken of an exemplary MR phantom apparatus in accordance with some embodiments of the present disclosure.
Figure 5:
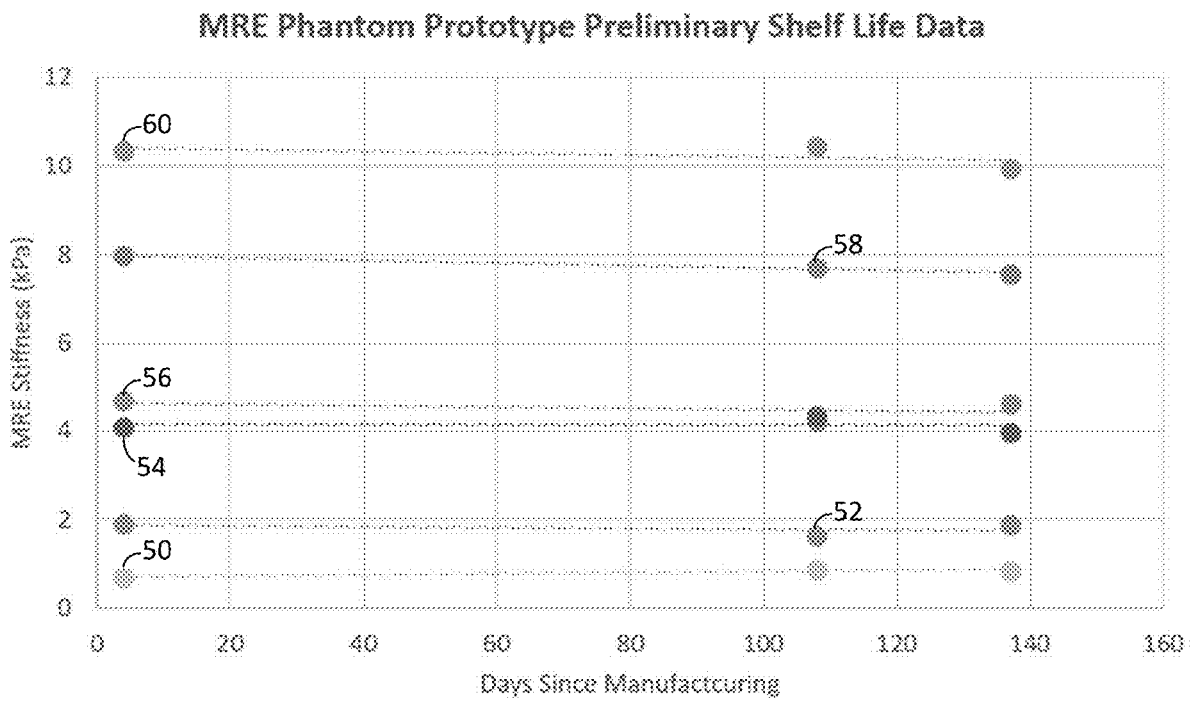
FIG. 5 is a graph of longitudinal stiffness measurements taken during magnetic resonance elastography excitations in accordance with some embodiments of the present disclosure.
Figure 6:
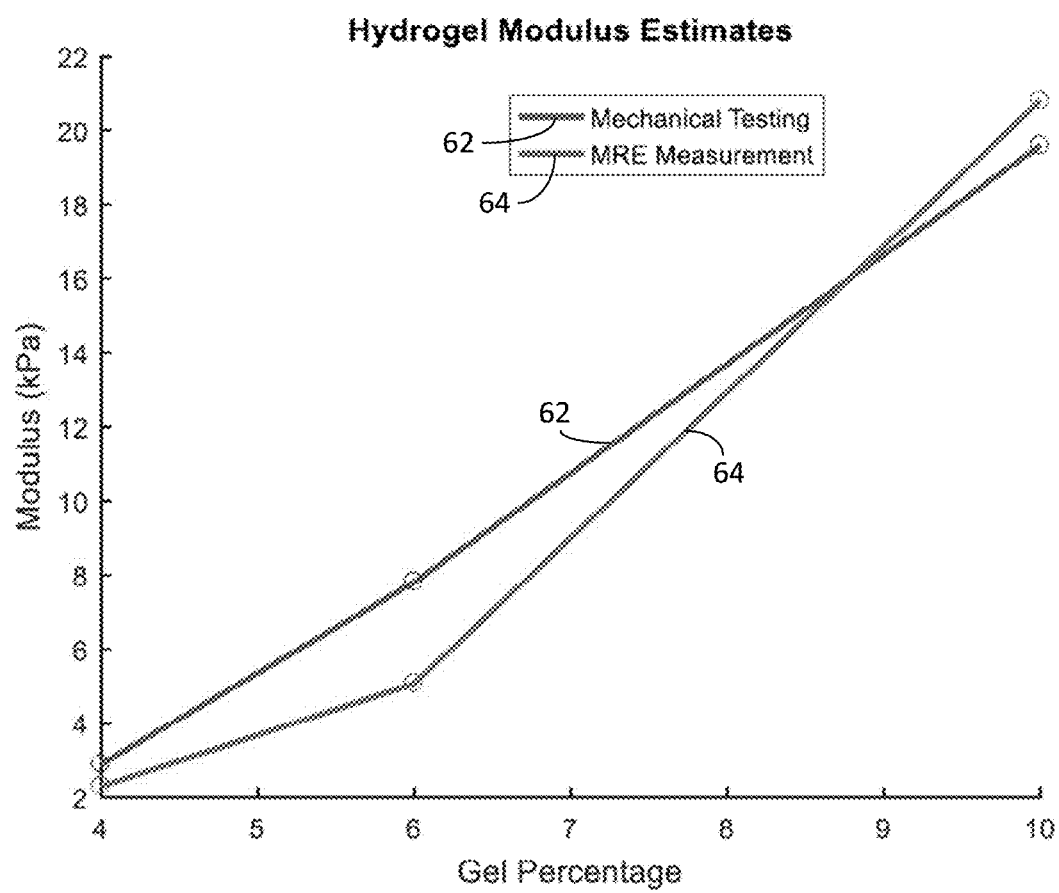
FIG. 6 is a graph of magnetic resonance elastography parameters taken of an exemplary MR phantom apparatus in accordance with some embodiments of the present disclosure.

Results/Discussion:

A MRE phantom prototype was successfully created and withstood mechanical MRE vibration in the full range of MRE excitations. MRE stiffness maps are shown in FIG. 4, and the longitudinal stiffness measurements are shown in FIG. 5. FIG. 5 shows acrylamide/N—N'-methylene-bisacrylamide hydrogels at a 3% wt % (base medium hydrogel) 50, 4 wt % (compartment hydrogel) 52, 6 wt % (base medium hydrogel) 54, 6 wt % (compartment hydrogel) 56, 8 wt % (compartment hydrogel) 58, and 10 wt % (compartment hydrogel) 60. MRE scanning on separate hydrogel samples, including a 10% gel sample created with rapid polymerization, produced material modulus results comparable to results produce by mechanical analysis (FIG. 6, mechanical testing 62, MRE measurement 64).

This example demonstrates a hydrogel-based MRE phantom with targeted material properties. The polyacrylamide gels used were highly adaptable within the desired tissue stiffness range. Furthermore, the high water content of these gels proved to be beneficial for general image quality. The acrylic phantom shell was also found to be beneficial, as it acted as a resonating excitation medium.

DWI Phantoms:

A diffusion phantom with 5 compartments of varied apparent diffusion coefficient (ADC) was fabricated with polyacrylamide hydrogel. The hydrogel material base solution was created by dissolving two polymer components-acrylamide and bis-acrylamide (Fisher Scientific, Hampton, N.H., USA)- into de-ionized water. The stiffness of the hydrogel samples was varied by changing the percentage of polymer components dissolved in the water base. Gel percentages of each sample included in the phantom were 8%, 15%, and 22%, and 30%. Cross-linking of the gel was initiated by the addition of Tetramethylethylenediamine (TEMED) and ammonium persulfate (Fisher Scientific, Hampton, N.H., USA).

Four hydrogel compartments were created by filling custom 3D-printed cylindrical molds with hydrogel of different stiffness properties. The four cylinders were placed in a sealed polypropylene housing and surrounded by a fifth hydrogel of 3% gel composition.

DWI Images:

Diffusion-weighted MRI images were obtained, and a wide range of diffusion values was quantified. A DWI pulse sequence applies diffusion sensitizing magnetic field gradients in selected directions during the MM measurement cycle to obtain MR images that have an image contrast related to the diffusion of water or other fluid molecules that occurred during the application of the diffusion gradients. Using these DWI images, an apparent diffusion coefficient (ADC) may be calculated for each voxel location in the reconstructed images.

Anthropomorphic Hydrogels

Figure 7:
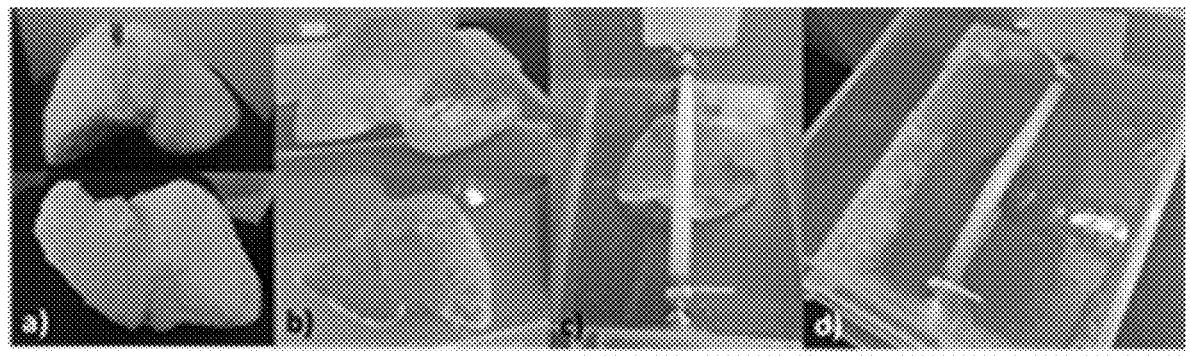
FIG. 7 is an example anthropomorphic hydrogel in the geometric shape of a liver in accordance of some embodiments of the present disclosure. The anthropomorphic motion phantom was created by a) designing a latex mold b) filling with hydrogel material and extracting a liver shaped volume c) fixing the hydrogel liver under a motion driver, and d) surrounding the liver with agar for improved imaging.

A hydrogel-based phantom was fabricated for testing motion-compensated diffusion MRI. This phantom consisted of an anthropomorphic hydrogel liver, an elastic tube motion driver, and agar, as shown in FIG. 7. To create the anthropomorphic hydrogel liver, a liver model was first 3D-printed with polyvinyl-alcohol (PVA) filament on an Ultimaker (Utrecht, Netherlands) S5 machine. The PVA liver was then coated in liquid latex rubber. Once the rubber coating had dried, the inner PVA liver volume was dissolved with water, leaving a liver-shaped void in a rubber shell. An 8% acrylamide/N—N'-methylene-bisacrylamide hydrogel concentration was then poured into the rubber mold and allowed to polymerize. Once cured, the hydrogel liver was extracted from the rubber, placed in a water-tight container, and surrounded with agar gel. Compliant tubing was then run over the top of the liver model and fixed within the water-tight container. The ends of the tubing were then integrated into a flow loop with a pulsatile positive displacement pump (BDC PD-1100, BDC Laboratories, Wheat Ridge, Colo.). Water was pumped through the system, causing deformation of the compliant tube and adjacent hydrogel liver model at a frequency of one hertz. This setup was intended to mimic the cyclic motion induced by the cardiac pulse near the top of the liver in-vivo. Both standard and motion-compensated diffusion imaging were performed.

Figure 8:
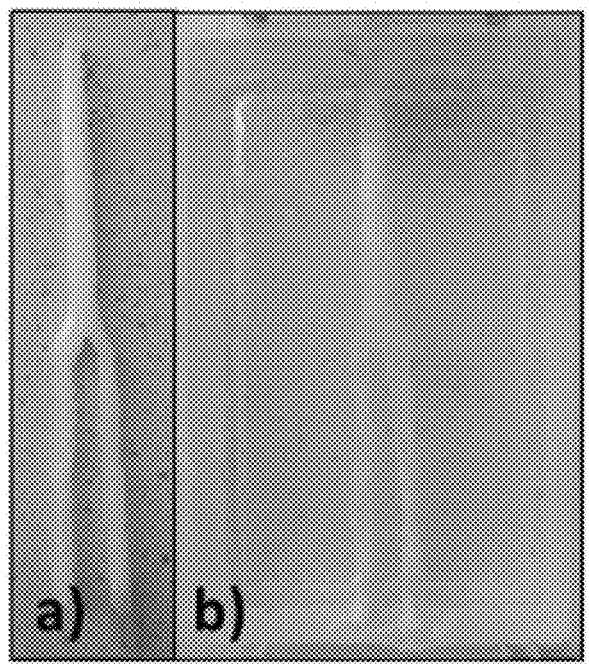
FIG. 8 is an example anthropomorphic hydrogel in a carotid bifurcation vessel geometry in accordance of some embodiments of the present disclosure. A) is the bifurcation core and b) is the finished hydrogel model with a vessel void.

FIG. 8 illustrates a 3D printed carotid bifurcation vessel geometry fabricated for PC MRI and blood vessel motion analysis. The printed geometry was coated with silicone and set in a hydrogel of 12% gel concentration using the method described for the liver hydrogel of FIG. 7. The vessel core was then dissolved from the hydrogel and fixed to the pulsatile pump system. 4D flow MRI and vessel displacement imaging were performed on the hydrogel model with a PC-VIPR.

The invention has been described according to one or more preferred embodiments, and it should be appreciated that many equivalents, alternatives, variations, and modifications, aside from those expressly stated, are possible and within the scope of the invention.

The preceding discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

It is to be understood that the disclosure is not limited in its application to the details of construction and the arrangement of components set forth in the description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

We claim:

1. A magnetic resonance phantom comprising:
   (i) a housing;
   (ii) a base medium disposed within the housing; and
   (iii) one or more compartment extending through the base medium, the one or more compartment comprising a crosslinked acrylamide-based polymer,
   wherein the crosslinked acrylamide-based polymer is composed of an acrylamide/crosslinking agent copolymer.

2. The magnetic resonance phantom of claim 1, wherein a polymerized acrylamide monomer constitutes at least 50 wt % based on the total weight of the acrylamide-based polymer.

3. The magnetic resonance phantom of claim 1, wherein a polymerized crosslinking comonomer constitutes less than 10 wt % based on the total weight of the acrylamide-based polymer.

4. The magnetic resonance phantom of claim 1, wherein the one or more compartment comprises a hydrogel, wherein the hydrogel comprises the crosslinked acrylamide-based polymer and a solvent or dispersing medium.

5. The magnetic resonance phantom of claim 4, wherein the solvent or dispersing medium constitutes at least 50 wt % based on the total weight of the hydrogel.

6. The magnetic resonance phantom of claim 4, wherein the acrylamide-based polymer constitutes less than 50 wt % based on the total weight of the hydrogel.

7. The magnetic resonance phantom of claim 4, wherein the hydrogel has one or more of the following properties:

(a) an apparent diffusion coefficient from 0.1 to $2.5 \times 10^{-3}$ mm$^2$/s; and (b) a material modulus from 1 kPa to 100 kPa.

8. The magnetic resonance phantom of claim 1 comprising from 2 to 50 compartments.

9. The magnetic resonance phantom of claim 8, wherein the compartments have a spacing from 1 mm to 100 mm.

10. The magnetic resonance phantom of claim 1, wherein the one or more compartments have a diameter from 5 mm to 500 mm.

11. The magnetic resonance phantom of claim 1, wherein the one or more compartments extend from 75% to 100% of the length or height of the housing.

12. The magnetic resonance phantom of claim 1 further comprising a plurality of compartments that form an array of acrylamide-based polymer concentrations that ranges from greater than, or equal to, 0 wt % to less than, or equal to, 50 wt % acrylamide-based polymer based on the total weight of components in each compartment in the array.

13. The magnetic resonance phantom of claim 1, wherein the one or more compartments constitutes from 5% to 95% (v/v) of the internal volume of the housing.

14. The magnetic resonance phantom of claim 1, wherein the base medium comprises a hydrogel.

15. The magnetic resonance phantom of claim 14, wherein the one or more compartment forms a cylindrical shape having a top face, a bottom face, and body section that extends between the top face and the bottom face, the body section having an ellipse cross section, and wherein the base medium completely surrounds the body section of the one or more compartment.

16. The magnetic resonance phantom of claim 1, wherein the housing includes a hemispherical portion, wherein the hemispherical portion includes recessed region sized to receive a passive driver for magnetic resonance elastography imaging, and wherein the recessed region includes an interior face that is configured to allow the passive driver to transmit mechanical waves to the one or more compartments during magnetic resonance elastography imaging.

17. A magnetic resonance phantom comprising:

a sealed compartment;

a hydrogel disposed in the sealed compartment, the hydrogel comprising a crosslinked acrylamide-based polymer and a solvent, the crosslinked acrylamide-based polymer comprising:

(i) at least 50 wt % of a polymerized acrylamide monomer, based on the total weight of the acrylamide-based polymer; and (ii) less than 10 wt % of a crosslinking agent, based on the total weight of the crosslinked acrylamide-based polymer.

18. The magnetic resonance phantom of claim 17, wherein the sealed compartment is composed of a material selected from the group consisting of a polymeric film and glass.

19. The magnetic resonance phantom of claim 17, wherein the hydrogel has an anthropomorphic shape.

20. A magnetic resonance phantom comprising:

(i) a housing;

(ii) a base medium disposed within the housing; and (iii) one or more compartment extending through the base medium, the one or more compartment comprising a crosslinked acrylamide-based polymer, wherein the one or more compartment comprises a hydrogel, wherein the hydrogel comprises the crosslinked acrylamide-based polymer and a solvent or dispersing medium.

21. A magnetic resonance phantom comprising:

(i) a housing;

(ii) a base medium disposed within the housing; and (iii) a plurality of compartments extending through the base medium, the plurality of compartments comprising a crosslinked acrylamide-based polymer, wherein the plurality of compartments form an array of acrylamide-based polymer concentrations that ranges from greater than, or equal to, 0 wt % to less than, or equal to, 50 wt % acrylamide-based polymer based on the total weight of components in each compartment in the array.

* * * * *

UNITED STATES PATENT AND TRADEMARK OFFICE
CERTIFICATE OF CORRECTION

PATENT NO. : 11,181,601 B1  
APPLICATION NO. : 16/878399  
DATED : November 23, 2021  
INVENTOR(S) : Alejandro Roldán-Alzate et al.

Page 1 of 1

It is certified that error appears in the above-identified patent and that said Letters Patent is hereby corrected as shown below:

In the Specification

Column 1, Line 30, "(MM)" should be --(MRI)--.

Column 1, Line 37, "MM" should be --MRI--.

Column 1, Line 43, "MM" should be --MRI--.

Column 5, Line 55, "MM" should be --MRI--.

Column 9, Line 6, "MM" should be --MRI--.

Column 11, Line 22, "MM" should be --MRI--.

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*